(12) United States Patent
Farr et al.

(10) Patent No.: US 10,603,290 B2
(45) Date of Patent: *Mar. 31, 2020

(54) FORMULATION FOR INHIBITING FORMATION OF 5-HT$_{2B}$ AGONISTS AND METHODS OF USING SAME

(71) Applicant: ZOGENIX INTERNATIONAL LIMITED, Berkshire (GB)

(72) Inventors: Stephen J. Farr, Orinda, CA (US); Brooks Boyd, Berkeley, CA (US)

(73) Assignee: ZOGENIX INTERNATIONAL LIMITED, Berkshire (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/193,812

(22) Filed: Nov. 16, 2018

(65) Prior Publication Data

US 2019/0083424 A1    Mar. 21, 2019

Related U.S. Application Data

(63) Continuation of application No. 15/667,112, filed on Aug. 2, 2017, now abandoned.

(60) Provisional application No. 62/379,183, filed on Aug. 24, 2016, provisional application No. 62/515,383, filed on Jun. 5, 2017.

(51) Int. Cl.
| | |
|---|---|
| *A61K 31/137* | (2006.01) |
| *A61K 45/06* | (2006.01) |
| *A61K 31/36* | (2006.01) |
| *A61K 31/551* | (2006.01) |
| *A61K 31/05* | (2006.01) |
| *A61K 31/105* | (2006.01) |

(52) U.S. Cl.
CPC .......... *A61K 31/137* (2013.01); *A61K 31/105* (2013.01); *A61K 31/36* (2013.01); *A61K 31/551* (2013.01); *A61K 45/06* (2013.01)

(58) Field of Classification Search
CPC ...... A61K 31/137; A61K 45/06; A61K 31/36; A61K 31/551; A61K 31/05
See application file for complete search history.

(56) References Cited

U.S. PATENT DOCUMENTS

| | | | |
|---|---|---|---|
| 4,452,815 A | 6/1984 | Wurtman | |
| 5,834,477 A | 11/1998 | Mioduszewski | |
| 5,985,880 A | 11/1999 | Chang | |
| 6,599,901 B1 | 7/2003 | Flohr | |
| 9,125,900 B2 | 9/2015 | Meyer | |
| 9,549,909 B2 | 1/2017 | Ceulemens | |
| 9,603,814 B2 | 3/2017 | Ceulemens | |
| 9,603,815 B2 | 3/2017 | Ceulemens | |
| 9,610,260 B2 | 4/2017 | Ceulemens | |
| 2003/0118654 A1 | 6/2003 | Santos et al. | |
| 2006/0121066 A1 | 6/2006 | Jaeger et al. | |
| 2006/0270611 A1 | 11/2006 | Dries et al. | |
| 2008/0261962 A1 | 10/2008 | Greer | |
| 2010/0298181 A1 | 11/2010 | Hanada et al. | |
| 2011/0092535 A1 | 4/2011 | Barnes et al. | |
| 2011/0212171 A1 | 9/2011 | Venkatesh et al. | |
| 2012/0115958 A1 | 5/2012 | Mariotti et al. | |
| 2012/0270848 A1 | 10/2012 | Mannion | |
| 2013/0296398 A1* | 11/2013 | Whalley | A61K 31/05 514/425 |
| 2014/0030343 A1 | 1/2014 | Lamson | |
| 2014/0162942 A1 | 6/2014 | Ghosal | |
| 2014/0329908 A1 | 11/2014 | Ceulemens et al. | |
| 2014/0343162 A1 | 11/2014 | Ceulemens et al. | |
| 2015/0080377 A1 | 3/2015 | Dhanoa | |
| 2015/0291597 A1 | 10/2015 | Mannion | |
| 2015/0359755 A1 | 12/2015 | Guy et al. | |
| 2016/0136114 A1 | 5/2016 | Ceulemens et al. | |
| 2017/0020885 A1 | 1/2017 | Hsu | |
| 2017/0056344 A1 | 3/2017 | Farr et al. | |
| 2017/0071949 A1 | 3/2017 | De Witte et al. | |
| 2017/0174613 A1 | 6/2017 | Londesbrough et al. | |
| 2017/0348303 A1 | 12/2017 | Bosse | |
| 2018/0028499 A1 | 2/2018 | Baraban et al. | |

(Continued)

FOREIGN PATENT DOCUMENTS

| | | |
|---|---|---|
| JP | H05-310564 A | 11/1993 |
| WO | WO 2005/004865 | 1/2005 |
| WO | WO 2008/025148 | 3/2008 |

(Continued)

OTHER PUBLICATIONS

Brunklaus et al., "Dravet syndrome—From epileptic encephalopathy to channelopathy" Epilepsia (May 16, 2014) 55(7):979-984.
Buchanan, Gordon F. et al., Serotonin neurones have anticonvulsant effects and reduce seizure-induced mortality, The Journal of Physiology, 2014, vol. 592, Issue 19, p. 4395-4410.
C. B. Catarino et al. "Dravet Syndrome as epileptic encephalopathy: Evidence from long-term course and neuropathology", Brain, vol. 134, No. 10 (Jun. 29, 2011) pp. 2982-3010.
Ceulemans et al., "Poster presented at the 69th Annual Meeting of the American Epilepsy Society" (Dec. 2015) Philadelphia.
Devinsky et al., "Trial of Cannabidiol for Drug-Resistant Seizures in the Dravet Syndrome" The New Engalnd Journal of Medicine (May 25, 2017) 376(21):2011-2020.

(Continued)

*Primary Examiner* — Shirley V Gembeh
(74) *Attorney, Agent, or Firm* — Karl Bozicevic; Bozicevic, Field & Francis LLP

(57) ABSTRACT

Drug combinations and their use are disclosed. A first drug is administered in combination with a second drug. The first drug such as fenfluramine is characterized by the formation of a metabolite including 5-HT$_{2B}$ agonists such as norfenfluramine with known adverse side effects. The second drug is in the form of a CYP inhibitor such as cannabidiol which modulates the formation of metabolite down thereby making the first drug safer.

10 Claims, 8 Drawing Sheets

(56) References Cited

U.S. PATENT DOCUMENTS

| | | |
|---|---|---|
| 2018/0141953 A1 | 5/2018 | Dax |
| 2018/0215701 A1 | 8/2018 | Carroll et al. |

FOREIGN PATENT DOCUMENTS

| | | |
|---|---|---|
| WO | WO 2014/177676 | 11/2014 |
| WO | WO 2015/026849 | 2/2015 |
| WO | WO 2015/066344 | 5/2015 |
| WO | WO 2015/193668 | 12/2015 |
| WO | WO 2016/138138 | 9/2016 |
| WO | WO 2017-035267 | 3/2017 |
| WO | WO 2018/037306 | 3/2018 |
| WO | WO 2018/060732 | 4/2018 |
| WO | WO 2018/206924 | 11/2018 |

OTHER PUBLICATIONS

Döring et al. "Thirty Years of Orphan Drug Legislation and the Development of Drugs to Treat Rare Seizure Conditions: A Cross Sectional Analysis" PLOS One, pp. 1-15 (Aug. 24, 2016).

Gastaut et al., "Compulsive respiratory sterotypies in children with autistic features: Polygraphic recording and treatment with fenfluramine" Journal of Autism and Developmental Disorders, (Sep. 1, 1987) 17(3):391-406.

Gioia et al., "Confirmatory Factor Analysis of the Behavior Rating Inventory of Executive Function (BRIEF) in a Clinical Sample" Child Neuropsychology (2002) 8(4):249-57.

Isaac, Methvin, Serotonergic 5-HT2C Receptors as a Potential Therapeutic Target for the Design Antiepileptic Drugs, Current Topics in Medicinal Chemistry, 2005, vol. 5, Issue 1, p. 59-67.

Klein, M. T. and Teitler, M. , Distribution of 5-htlE receptors in the mammalian brain and cerebral vasculature: an immunohistochemical and pharmacological study, British Journal of Pharmacology, Jun. 2012, vol. 166, No. 4, p. 1290-1302.

Leit, Silvana et al., Design and synthesis of tryptamine-based 5HT2C agonists for the treatment of certain CNS disorders, Division of Medicinal Chemistry Scientific Abstracts for the 240th National ACS Meeting and Exposition, Jul. 28, 2010, MEDI367.

LeJeune et al, "Psychometric Support for an Abbreviated Version of the Behavior Rating Inventory of Executive Function (BRIEF) Parent Form" Child Neuropsychology (2010 16:182-201.

NCT02682927 (Sep. 3, 2016, 10 pages) Accessed from https://www.clinicaltrials.gov/ct2/history/NCT02682927?V_=View#StudyPageTop on Mar. 18, 2019).

Pittala, Valeria et al., 5-HT7 Receptor Ligands: Recent Developments and Potential Therapeutic Applications, Mini-Reviews in Medicinal Chemistry, 2007, vol. 7, Issue 9, p. 945-960.

Schoonjans et al. "Low-dose fenfluramine significantly reduces seizure frequency in Dravet syndrome: a prospective study of a new cohort of patients", European Journal of Neurology, vol. 24, No. 2, (Oct. 28, 2016), pp. 309-314.

Viola et al., "The Behavior Rating Inventory of Executive Function (BRIEF) to Identify Pediatric Acute Lymphoblastic Leukemia (ALL) Survivors at Risk for Neurocognitive Impairment" Journal of Pediatric Hematology/Oncology (Apr. 1, 2017) 39(3):174-178.

Wirrell et al., "Optimizing the Diagnosis and Management of Dravet Syndrome: Recommendations From a North American Consensus Panel" Pediatric Neurology (Mar. 2017) 68:18-34.

Wurtman et al., "Fenfluramine and other serotoninergic drugs depress food intake and carbohydrate consumption while sparing protein consumption" Current Medical Research and Opinion (1979) 6(1 Supp):28-33.

Anandam, R., Affiliations Indian Journal of Pediatrics (Jan. 1, 2000) 67 (1 Suppl):S88-91 (Abstract Only).

Anonymous, "Determination That Pondimin (Fenfluramine Hydrochloride) Tablets, 20 Milligrams and 60 Milligrams, and Ponderex (Fenfluramine Hydrochloride) Capsules, 20 Milligrams Were Withdrawn From Sale for Reasons of Safety or Effectiveness".

Anonymous, "MacReportMedia—Brabant Pharma Reports Two-Year Follow-up Data From a 19-year Observational Study Using Low-Dose Fenfluramine for the Treatment of Dravet Syndrome", Nov. 25, 2013 (Nov. 25, 2013).

Arzimanoglou, "Dravet syndrome: From electroclinical characteristics to molecular biology" Epilepsia, 50(Suppl. 8):3-9 (2009).

Boel and Casaer et al., "Add-on Therapy of Fenfluramine in Intractable Self-Induced Epilepsy" Neuropaediatrics 1996, 27(4):171-173.

Brunklaus et al., "Prognostic, clinical and demographic features in SCN1A mutation-positive Dravet syndrome" Brain, 2012, p. 1-8.

Carvalho et al., "d-Amphetamine Interaction with Glutathione in Freshly Isolated Rat Hepatocytes" Chemical Research in Toxicology (Jan. 1996) 9(6):1031-1036.

Casaer et al., "Fenfluramine as a Potential Antiepileptic Drug" Epilepsia, 43(2), 205-206, 2002.

C. Doege et al., "Myoclonic-astatic epilepsy: Doose-Syndrum 2014: Doose syndrome 2014", Zeitschrift FR Epileptologie, (Mar. 20, 2014).

Ceulemans et al., "Successful use of fenfluramine as an add-on treatment for Dravet syndrome" Epilepsia, 53(7), 2012, 1131-1139.

Ceulemans, "Overall management of patients with Dravet syndrome" Developmental Medicine & Child Neurology, 2011, 53, 19-23.

Ceulemans B. et al., "Successful use of Fenflurarmine as add-on treatment in Dravet syndrome: a two year prospective follow up", European Journal of Paediatric Neurology, vol. 17, 01101866, Sep. 1, 2013 (Sep. 1, 2013).

Ceulemans B., "Successful Use of Fenfluramine as Add-On Treatment in Dravet Syndrome" Epilepsia, 52(Suppl. 6):4-22 (2011).

Ceulemans et al., "Five-year extended follow-up status of 10 patients with Dravet syndrome treated with fenfluramine" Epilepsia (May 20, 2016) 57(7):e129-e134.

Chiron et. al., "The pharmacologic treatment of Dravet syndrome" Epilepsia (2011) 52(Suppl 2):72-75.

Clemens B., "Dopamine agonist treatment of self-induced pattern-sensitive epilepsy. A case Report" Epilepsy Res. 2. 1988, p. 340-343.

Curzon et al., "Appetite suppression by commonly used drugs depends on 5-HT receptors but not on 5-HT availability" Tips (1997) 18:21-25.

Franco-Perez, Javier "The Selective Serotonin Reuptake Inhibitors: Antidepressants with Anticonvulsant Effects?" Ann Deoress Anxiety (2014) 1(5):1025 (2 pages).

K Gentsch et al., "Laboratory Research Fenfluramine Blocks Low-Mg2'-Induced Epileptiform Activity in Rat Entorhinal Cortex" Epilepsia, Jan. 1, 2000 (Jan. 1, 2000), pp. 41(8):925-928.

Gharedaghi et al., "The role of different serotonin receptor subtypes in seizure susceptibility" Exp. Brain Res (2014) 232:347-367.

Habibi et al., "The Impact of Psychoactive Drugs on Seizures and Antiepileptic Drugs" Current Neurology and Neuroscience Reports (Jun. 17, 2016) 16(8):1-10.

Haritos et al., "Metabolism of dexfenfluramine in human liver microsomes and by recombinant enzymes: Role of CYP2D6 and 1A2" Pharmcogenetics (Oct. 1998) 8(5):423-432.

Harvard Health Publishing, Harvard Medical School Generalized Seizures (Grand Mal Seizures) (Apr. 2014) pp. 1-5 (https://www.health.hearvard.edu/diseases-and-conditions/generalized-seizures-grand-mal-se . . .).

Hazai et al., "Reduction of toxic metabolite formation of acetaminophen" Biochemical and Biophysical Research Communications (Mar. 8, 2002) 291(4):1089-1094.

Hegadoren et al., "Interactions of iprindole with fenfluramine metabolism in rat brain and liver" Journal of Psychiatry & Neuroscience (Mar. 1991) pp. 5-11.

Katholieke Universiteit Leuven, University Hospital Antwerp: "Interim results of a fenfluramine open-label extension study", European Patent Register (May 25, 2017).

Lagae et al. "A pilot, open-label study of the effectiveness and tolerability of low-dose ZX008 (fenfluramine HC1) in Lennox-Gastaut syndrome" Epilepsia (2018) 59: 1881-1888.

(56) References Cited

OTHER PUBLICATIONS

Lopez-Meraz et al., "5-$HT_{1A}$ receptor agonist modify epileptic seizures in three experimental models in rats" Neuropharmacology (2005) 49:367-375.
Martin, et al., "An Examination of the Mechanism of Action of Fenfluramine in Dravet Syndrome: A Look Beyond Serotonin" Presented as part of the Zogenix Scientific Exhibit During the 70$^{th}$ Annual Meeting of the American Epilepsy Society, Houston, Texas.
Meador K J., "Seizure reduction with fluoxetin in an adult woman with Dravet syndrome", Epilepsy & Behavior Case Reports, Elsevier BV, NL, vol. 2, Jan. 1, 2014 (Jan. 1, 2014), pp. 54-56.
Mudigoudar et al., "Emerging Antiepileptic Drugs for Severe Pediatric Epilepsies" Seminars in Pediatric Neurology (Jun. 2016) 23(2):167-179.
Mulley et al., "SCN1A Mutations and Epilepsy" Human Mutation (2005) 25:535-542.
Naithani et al., "The Conventional Antiepileptic Drug Use When Compared to a Combination Therapy Regime in a Teaching Hospital in India" International Journal of Pharma and Bio Sciences (2012) 3(1):B-191-B-197.
Nozulak et al., "(+)-cis-4,5,7a,8,9,10,11,11a-Octahydro-7H-10-methylindolo[1,7-bc][2,6]-naphthridine: A 5-$HT_{2C/2B}$ Receptor Antagonist with Low 5-$HT_{2A}$ Receptor Affinity" J. Med. Chem. (1995) 38:28-33.
O'Neill et al., "GR46611 potentiates 5-$HT_{1A}$ receptor-mediated locomotor activity in the guinea pig" European Journal of Pharmacology (1999) 370:85-92.
Pirincci et al., "The Effects of Fenfluramine on Blood and Tissue Seratonin (5-Hydroxytryptamine) Levels in Rats" Turk J Vet Anim Sci (2005) 29:857-863.
Remington, "The Science and Practice of Pharmacy", Nineteenth Edition (1995), pp. 710-712.
Rho, Jong M. "Basic Science Behind the Catastrophic Epilepsies" Epilepsia (2004) 45(Suppl. 5):5-11.
Rothman et al., "Serotonergic drugs and valvular heart disease" Expert Opinion on Drug Safety (May 2009) 8(3):317-329.
Schoonjans, An-Sofie "Low-dose fenfluramine in the treatment of neurologic disorders: experience in Dravet syndrome" Therapeutic Advances in Neurological Disorders (Jan. 1, 2015) pp. 328-338.
Sourbron et al., "Serotonergic Modulation as Effective Treatment for Dravet Syndrome in Zebrafish Mutant Model" ACS Chemical Neuroscience (Feb. 17, 2016) 7(5):588-598.
Sharma et al. Indian Journal of Pharmacology, 1996, 28(1), 1-10.
Sullivan et al. "Effect of ZX008 (fenfluramine HCl oral solution) on total seizures in Dravet syndrome" Neurology: Official Journal of the American Academy of Neurology, 2018, 90(24):e2187-e2811.
Vickers et al., "Oral Administration of the 5-HT2C receptor agonist, mCPP, reduces body weight gain in rats over 28 days as a result of maintained hypophagia" Psychopharmacology (May 2003), 167 (3): 274-280.
Wirrell et al., "Stiripentol in Dravet syndrome: Results of a retrospective U.S. study" Epilepsia (2013) 54(9):1595-1604.
Yamaori et al., "Potent inhibition of human cytochrome P450 3A isoforms by cannabidiol: Role of phenolic hydroxyl groups in the resorcinol moiety" Life Sciences (2011) 88:730-736.
Yoshida et al. (2017), "Impact of Physiologically Based Pharmacokinetic Models on Regulatory Reviews and Product Labels: Frequent Utilization in the Field of Oncology" in Clinical Pharmacology and Therapeutics 2017; 101(5): 597-602.
Zhang et al., *A Physiological-based Pharmacokinetic (PBPK) Modeling Approach to Quantifying Drug-Drug Interactions: Applications to the Development of Fenfluramine (ZX008) for Treatment of Seizures in Dravet Syndrome (DS)*. Presented at the 2016.
Zhang et al., A Physiological-based Pharmacokinetic (PBPK) Modeling Approach to Quantifying Drug-Drug Interactions: Applications to the Development of Fenfluramine (ZX008) for Treatment of Seizures in Dravet Syndrome (DS). Published in Abstracts.
Zhuang et al. (2016), "PBPK modeling and simulation in drug research and development" in Acta Pharmaceutica Sinica B 2016;6(5):430-440.
Zogenix "Corporate Update Nasdaq: ZGNX" (Jun. 1, 2016) Retrieved from the Internet: URL:http://www.jefferies.com/CMSFiles/Jefferies.com/files/Conferences/060716/Presentations/Zogenix%20Inc.pdf [retrieved on Feb. 21, 2018].
Faingold et al., "Prevention of seizure-induced sudden death in a chronic SUDEP model by semichronic administration of a selective serotonin reuptake inhibitor" Epilepsy & Behavior (2011) 22:186-190.
Manzke et al., "5-HT4(a) receptors avert opiod-induced breathing depression without loss of analgesia" Science (Jul. 11, 2003) 301:226-229.
Wallace et al., "Pharmacotherapy for Dravet Syndrome" Paediatr. Drugs, 18(3):197-208 (Jun. 2016).
Wirrell et al., "Stiripentol in Dravet Syndrome: Is it Worth It?" Epilepsy Currents, 14(1):22-23 (Jan./Feb. 2014).
Wirrell et al., "Treatment of Dravet Syndrome" Can. J. Neurol. Sci., 43(Suppl. 3):513-18 (Jun. 2016).
F Brenot et al., "Primary Pulmonary Hypertension and Fenfluramine Use.", HEART, vol. 70, No. 6, Dec. 1, 1993 (Dec. 1, 1993), pp. 537-541.
Favale et al., "The anticonvulsant effect of citalopram as indirect evidence of serotonergic impairment in human epileptogenesis" Seizure (2003) 12:316-319.
Jake Remaly: "Fenfluramine Reduces Convulsive Seizure Frequency in Dravet Syndrome. Epilepsy Resource Center", Jan. 1, 2018 (Jan. 1, 2018).
An-Sofie Schoonjans et al: "Cardiovascular Safety of Low-Dose Fenfluramine in Dravet Syndrome: A Review of its Benefit-Risk Profile in a New Patient Population", Current Medical Research and Opinion, vol. 33, No. 10, Jul. 31, 2017 (Jul. 31, 2017), pp. 1773-1781.

\* cited by examiner

FIG. 1

| Study Day | -28 to -2 | -1 | 1 | | | | | | | | | | | | | | 2 | | 3 | 4 | Follow-up |
|---|---|---|---|---|---|---|---|---|---|---|---|---|---|---|---|---|---|---|---|---|---|
| | Screening | Admission | \multicolumn{16}{c}{Times After Dosing (h)} | | | | |
| | | | Pre-dose | 0 | 0.25 | 0.5 | 0.75 | 1 | 1.5 | 2 | 2.5 | 3 | 4 | 6 | 9 | 12 | 24 | 36 | 48 | 72 | Follow-up Call |
| General Assessments | | | | | | | | | | | | | | | | | | | | | |
| Informed Consent | X | | | | | | | | | | | | | | | | | | | | |
| Inclusion/Exclusion | X | X | | | | | | | | | | | | | | | | | | | |
| Medical History | X | X | | | | | | | | | | | | | | | | | | | |
| Weight, Height and BMI | X | X | | | | | | | | | | | | | | | | | | | |
| Vein Assessment | X | | | | | | | | | | | | | | | | | | | | |
| Carbon Monoxide Breath Test | X | X | | | | | | | | | | | | | | | | | | | |
| Drug Screen | X | X | | | | | | | | | | | | | | | | | | | |
| Alcohol breath Test | X | X | | | | | | | | | | | | | | | | | | | |
| FSH Test (Post-Menopausal Women) | X | | | | | | | | | | | | | | | | | | | | |
| CYP2D6 Genotyping (Period 1 only) | | | X | | | | | | | | | | | | | | | | | | |
| IMP Administration | | | | X | | | | | | | | | | | | | | | | | |
| Safety Assessments | | | | | | | | | | | | | | | | | | | | | |
| Urine Pregnancy Test | X | X | | | | | | | | | | | | | | | | | | | |
| Physical Examination | X | X | | | | | | | | | | | | | | | | | | | |
| Safety Labs | X | | X | | | | | | | | | | | | | | X | | X | X | |
| C-SSRS | X | | | | | | | | | | | | | | | | | | X | X | |
| Urinalysis | X | X | | | | | | | | | | | | | | | | | | | |
| ECG | X | | | | | | | | | | | | | | | | | | | | |
| Vital Signs | X | X | X | | | | | X | | | | | X | X | X | X | X | X | X | X | |
| Adverse Events | ←─────────────────────────────────────────────→ | | | | | | | | | | | | | | | | | | | | |
| Concomitant Medications | X | ←─────────────────────────────────────────────→ | | | | | | | | | | | | | | | | | | | X |
| PK Assessments | | | | | | | | | | | | | | | | | | | | | |
| Plasma Samples | | | X | | X | X | X | X | X | X | X | X | X | X | X | X | X | X | X | X | |

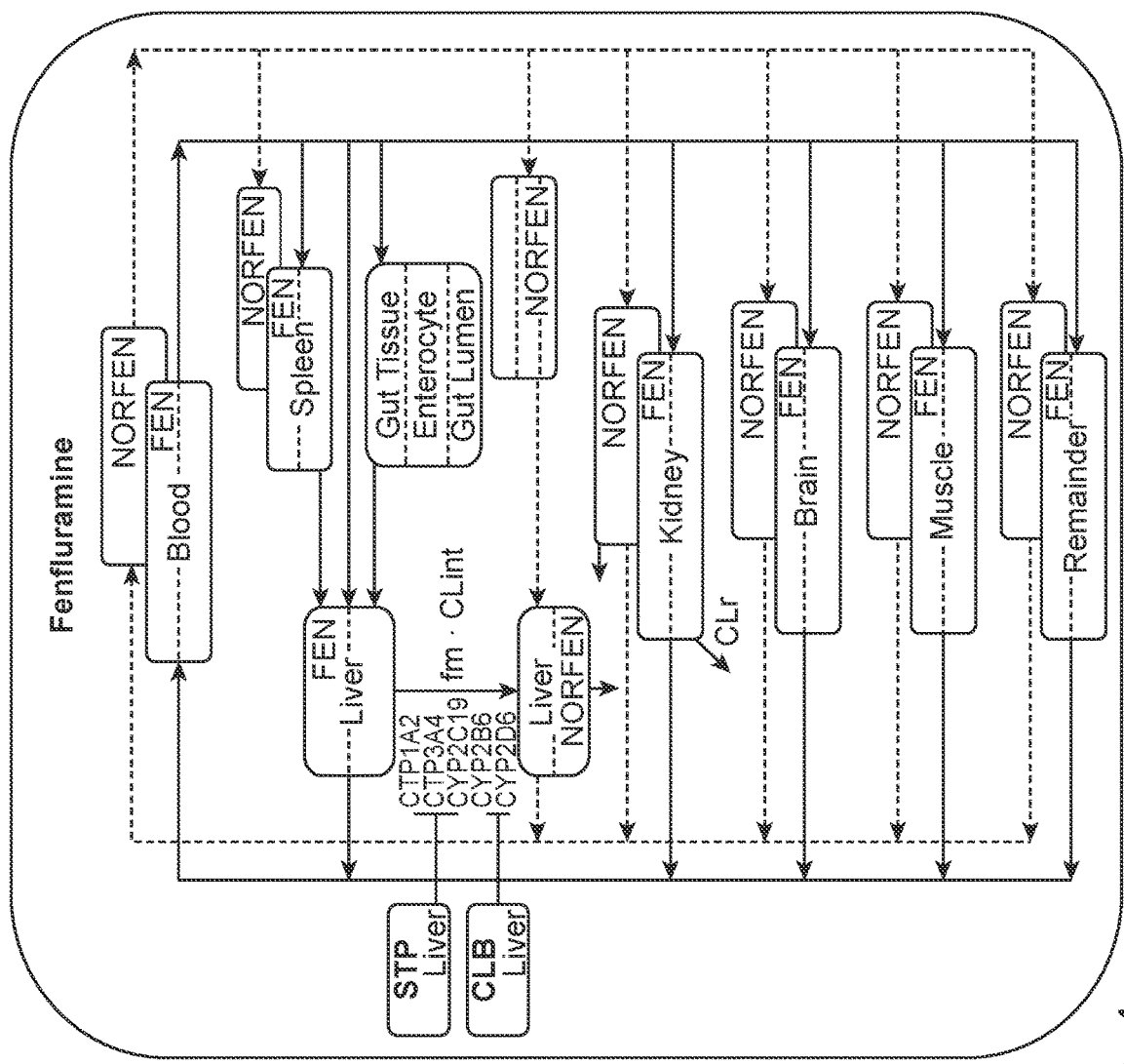
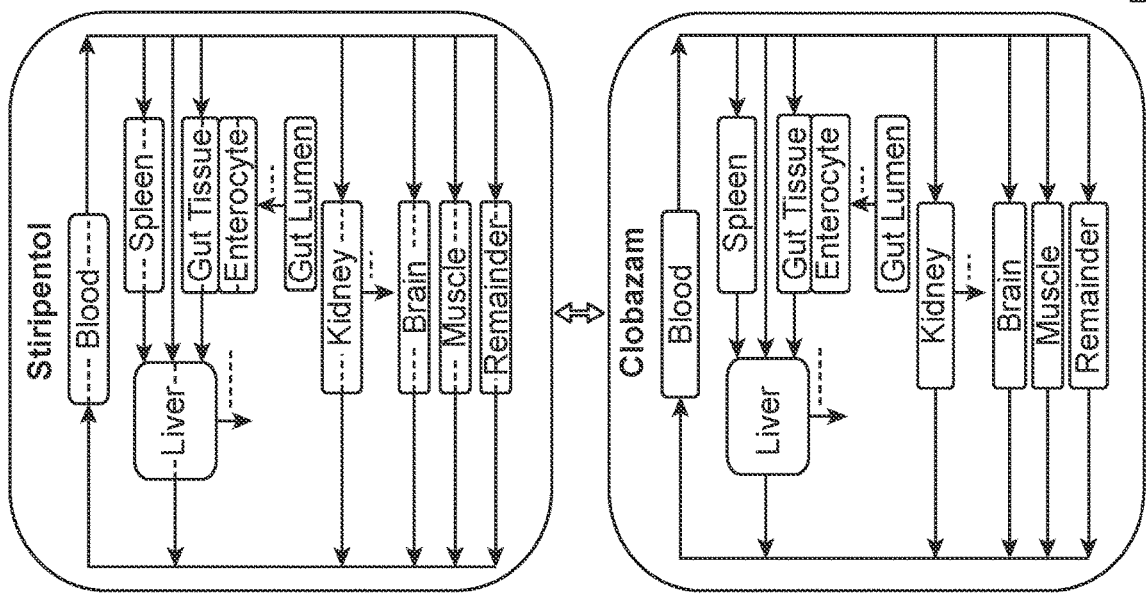
FIG. 4

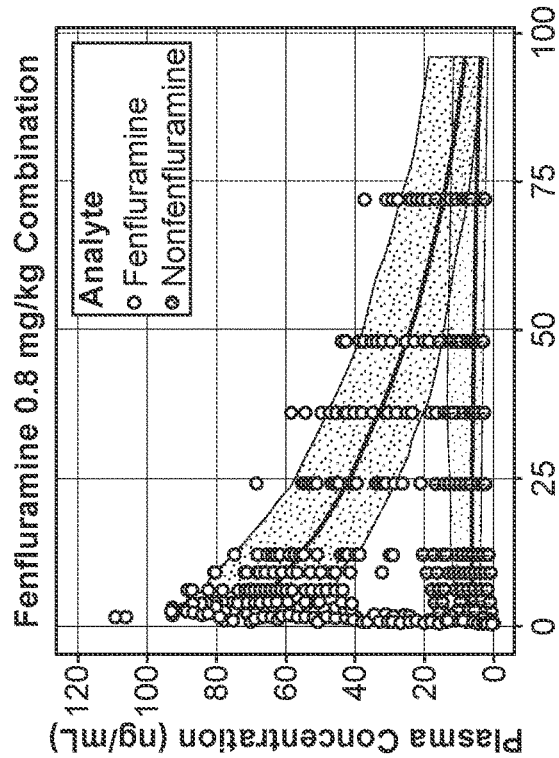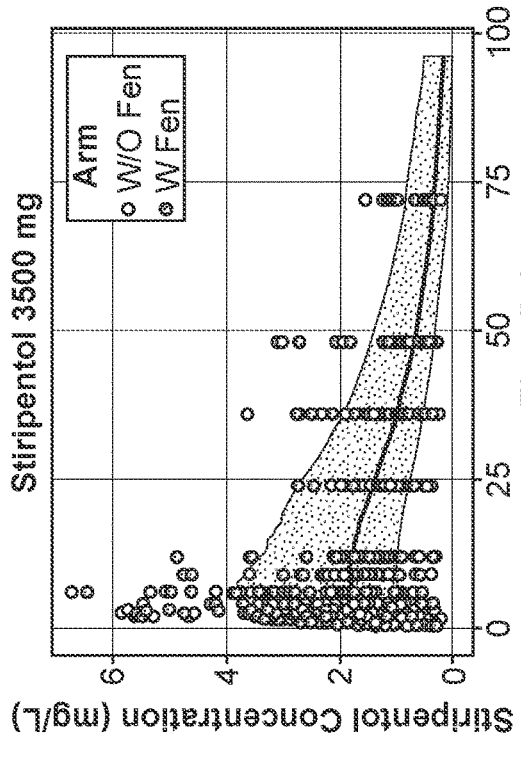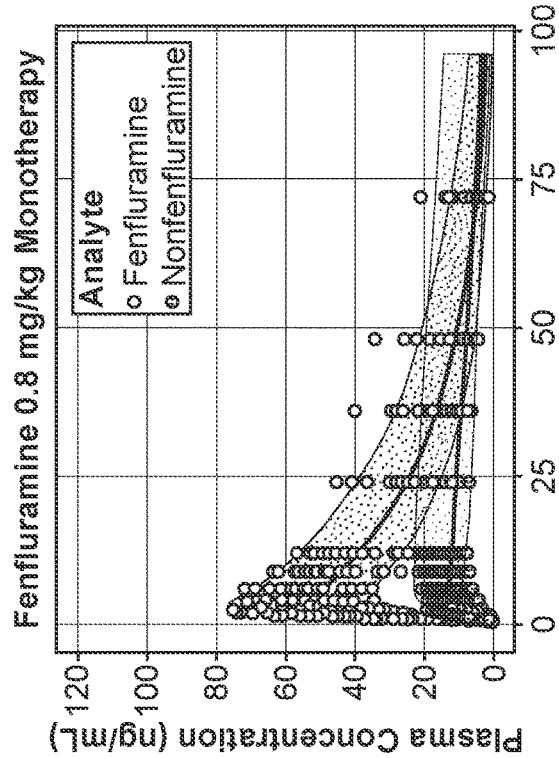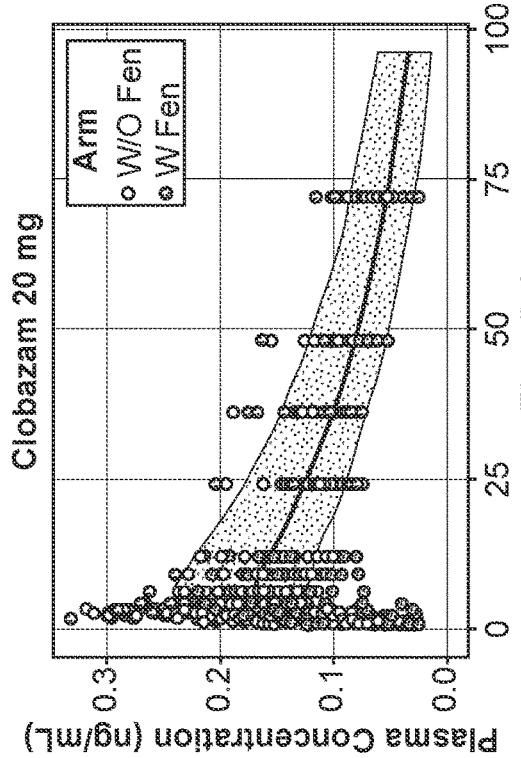

Fenfluramine

| Pathway | Clearance | Inhibition | Induction |
|---|---|---|---|
| CYP1A2 | ++ | | |
| CYP2B6 | ++ | | 1 |
| CYP2C9 | + | | |
| CYP2C19 | + | | |
| CYP2D6 | ++ | 1 | |
| CYP3A4 | + | | 1 |
| Renal | ++ | | |

FIG. 7A

Norfenfluramine

| Pathway | Clearance | Inhibition | Induction |
|---|---|---|---|
| CYP2B6 | | | 1 |
| CYP2D6 | | 1 | |
| CYP3A4 | | | 1 |

FIG. 7B

Clobazam

| Pathway | Clearance | Inhibition | Induction |
|---|---|---|---|
| CYP2B6 | + | | |
| CYP2C19 | + | | |
| CYP2D6 | | 2 | |
| CYP3A4 | ++ | | 1 |
| Renal | ++ | | |

FIG. 7D

N-desmethylclobazam

| Pathway | Clearance | Inhibition | Induction |
|---|---|---|---|
| CYP2C9 | | 1 | |
| CYP2C19 | ++ | | |
| CYP3A4 | | | 1 |
| UGT1A4 | | 1 | |
| UGT1A6 | | 1 | |
| UGT2B4 | | 1 | |
| Renal | ++ | | |

FIG. 7E

Stiripentol clearance pathway profile

| Pathway | Clearance | Inhibition | Induction |
|---|---|---|---|
| CYP1A2 | + | 2 | |
| CYP2B6 | | 2 | |
| CYP2C9 | | 1 | Unknown |
| CYP2C19 | + (invivo) | 1 | |
| CYP2D6 | | 2 | |
| CYP3A4 | | 2 | 1 |
| Renal and glucuronides | ++ (invivo) | | |

FIG. 7C

Cannabidiol clearance pathway profile

| Pathway | Clearance | Inhibition | Induction |
|---|---|---|---|
| CYP1A2 | | 2 (time dependent) | |
| CYP2B6 | | 2 | |
| CYP2C8 | | 1 | None (upto 1 µM) |
| CYP2C9 | + | 1 | |
| CYP2C19 | + | 1 | |
| CYP2D6 | | 1 | |
| CYP3A4 | ++ | 2 | |

FIG. 7F

FORMULATION FOR INHIBITING FORMATION OF 5-HT$_{2B}$ AGONISTS AND METHODS OF USING SAME

FIELD OF THE INVENTION

This invention relates generally to the field of pharmaceutical chemistry and more particular to drug combinations which inhibit the formation of metabolites which act on a 5-HT$_{2B}$ receptor and thereby reduce adverse side effects; and more particularly the combination of fenfluramine with drugs that inhibit the formation of norfenfluramine.

BACKGROUND OF THE INVENTION

Drug discovery to identify antiepileptic drugs that are effective against refractory epilepsies is a formidable challenge. The underlying etiologies are varied and are poorly understood. Many anti-epileptic drugs ("AEDs") are ineffective, or even contraindicated because they exacerbate symptoms. Often their mechanisms of action can be complex and are often incompletely characterized. Hence it is difficult to predict the efficacy of new drugs, even those that are structurally related to drugs known to work. A further difficulty is that patients who enroll in clinical trials are often being treated with multiple drugs which, while not eliminating seizures, keep them relatively stable. The ability to modify their treatment is sharply limited, owing to the risk that their condition will deteriorate and severe, often life-threatening symptoms will recur.

Nonetheless, there have been breakthroughs. An important one is fenfluramine, which is proving highly effective in treating refractory epilepsies, including Dravet syndrome, Lennox-Gastaut syndrome, Doose syndrome, and West syndrome. Dravet Syndrome, or severe myoclonic epilepsy in infancy, is a rare and malignant epileptic syndrome. This type of epilepsy has an early onset in previously healthy children, and is refractory to most conventional AEDs. Similarly, Lennox-Gastaut syndrome, Doose syndrome, and West syndrome are all severe diseases which are similarly refractory to conventional treatments. Prior to fenfluramine, there were few treatment options for any of those conditions which were reliably effective, and none that could eliminate seizures entirely for extended periods.

Fenfluramine, also known as 3-trifluoromethyl-N-ethyl-amphetamine, is the racemic mixture of two enantiomers, dexfenfluramine and levofenfluramine. While the mechanism by which it reduces seizures is not completely understood, fenfluramine increases the level of serotonin, a neurotransmitter that regulates mood, appetite and other functions. It causes the release of serotonin by disrupting vesicular storage of the neurotransmitter, and reversing serotonin transporter function. It is also known to act directly on 5HT receptors, particularly 5HT1D, 5HT2A, 5HT2C and 5HT7. It does not have significant agonistic effects on the 5HT2B receptor.

Fenfluramine is cleared from the plasma by renal excretion and through hepatic metabolism into norfenfluramine by cytochrome P450 enzymes in the liver, primarily CYP1A2, CYP2B6 and CYP2D6, but CYP2C9, CYP2C19 and CYP3A4 also contribute to fenfluramine clearance. See FIG. 7A. Such metabolism includes cleavage of an N-ethyl group by CYP450 enzymes to produce de-ethylated norfenfluramine metabolites such as norfenfluramine as shown below.

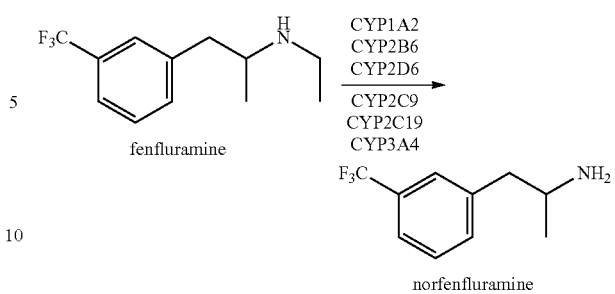

Fenfluramine was originally marketed as an anorectic agent under the brand names Pondimin, Ponderax and Adifax, but was withdrawn from the U.S. market in 1997 after reports of heart valve disease and pulmonary hypertension, including a condition known as cardiac fibrosis. It was subsequently withdrawn from other markets around the world. The distinctive valvular abnormality seen with fenfluramine is a thickening of the leaflet and chordae tendineae.

One mechanism used to explain this phenomenon involves heart valve serotonin receptors, which are thought to help regulate growth. 5-HT2B receptors are plentiful in human cardiac valves. Since fenfluramine and its active metabolite norfenfluramine stimulate serotonin receptors, with norfenfluramine being a particularly potent 5-HT2B agonist, this may have led to the valvular abnormalities found in patients using fenfluramine. Supporting this idea is the fact that this valve abnormality has also occurred in patients using other drugs that act on 5-HT2B receptors.

More generally, many highly effective drugs are, like fenfluramine, associated with significant risks owing to active metabolites which have toxic effects. The nature and severity of those risks strongly impact a drug's viability as a therapeutic agent, as well as its marketability, and there are many examples of highly effective drugs that were withdrawn due to safety concerns.

There is therefore a need in the art for methods of using fenfluramine to treat diseases and conditions responsive to fenfluramine that reduce the patient's exposure to harmful metabolites while maintaining therapeutically effective levels of fenfluramine. There is also a need in the art for new treatments for refractory pediatric epilepsy syndromes which are safe and effective.

SUMMARY OF THE INVENTION

Provided herein are compositions and methods for reducing exposure of a patient to harmful metabolites of a drug being used to treat that patient. For example, the disclosure provides methods and compositions for reducing exposure to a drug metabolite with potentially harmful activity mediated by a 5-HT$_{2B}$ receptor.

In one aspect, the disclosure provides methods of inhibiting the production of harmful metabolites in a subject being treated with a drug that is metabolized into one or more harmful metabolites, wherein the drug is coadministered with one or more metabolic inhibitors.

In one embodiment, the drug is fenfluramine or a pharmaceutically acceptable salt thereof, and is coadministered with a metabolic inhibitor such as cannabidiol.

In alternate embodiments, the drug, such as fenfluramine, is coadministered with one or more metabolic inhibitors selected from inhibitors of one or more metabolic enzymes selected from the group consisting of CYP1A2, CYP2B6, CYP2C9, CYP2C19, CYP2D6, and CYP3A4.

In alternate embodiments of this aspect, fenfluramine or a pharmaceutically acceptable salt thereof is co-administered with one or more agents selected from the group comprising stiripentol, clobazam and cannabidiol.

In alternate exemplary embodiments, fenfluramine or a pharmaceutically acceptable salt thereof is co-administered with stiripentol, or with cannabidiol, or with clobazam.

In alternate exemplary embodiments, the fenfluramine or a pharmaceutically acceptable salt thereof is co-administered with cannabidiol and stiripentol, or cannabidiol and clobazam, or stiripentol and clobazam.

In one exemplary embodiment, a fenfluramine active agent is co-administered with all of stiripentol, cannabidiol, and clobazam.

In another aspect, the disclosure provides methods of treating epilepsy or a neurological related disease by co-administering to a subject fenfluramine or a pharmaceutically acceptable salt thereof in combination with an effective amount of one or more metabolic inhibitors.

In alternate embodiments, the neurological related disease is Dravet syndrome, or is Lennox Gastaut syndrome, or is Doose syndrome, or is West syndrome In another aspect, the disclosure provides methods of suppressing appetite in a subject by coadministering to a subject fenfluramine or a pharmaceutically acceptable salt thereof in combination with an effective amount of one or more metabolic inhibitors.

Pharmaceutical compositions for use in practicing the subject methods are also provided.

An aspect of the invention in a method of reducing a therapeutic dose of fenfluramine, comprising:
  administering fenfluramine to a patient; and
  administering cannabidiol to the patient,
  whereby fenfluramine is administered in an amount which is at least 20% less than a therapeutic dose required when treating the patient for an indication being treated.

The above aspect of the invention includes an embodiment wherein the amount of fenfluramine administered is at least 30% less.

The above aspect of the invention includes an embodiment wherein the amount of fenfluramine administered is at least 40% less.

The above aspect of the invention includes an embodiment wherein the amount of fenfluramine administered is at least 50% less.

The above aspect of the invention includes an embodiment wherein the amount of fenfluramine administered is at least 60% less.

The above aspect of the invention includes an embodiment wherein the amount of fenfluramine administered is at least 70% less.

The above aspect of the invention includes an embodiment wherein the amount of fenfluramine administered is at least 80% less.

The above aspect of the invention includes an embodiment wherein the amount of fenfluramine administered is at least 90% less.

The above aspect of the invention includes an embodiment wherein the indication be treated is appetite suppression.

The above aspect of the invention includes an embodiment wherein the indication be treated is a refractory epilepsy.

The above aspect of the invention includes an embodiment wherein the refractory epilepsy selected is from the group consisting of Dravet syndrome, Lennox-Gastaut syndrome, and Doose syndrome.

An aspect of the invention is a method of reducing a therapeutic dose of a first drug, comprising:
  administering the first drug to a patient; and
  administering a second drug which is a CYP450 enzyme inhibitor to the patient,
  whereby first drug is administered in an amount which is at least 20% less than a therapeutic dose required when treating the patient for an indication being treated.

The above aspect of the invention includes an embodiment wherein the amount of first drug administered is at least 30% less.

The above aspect of the invention includes an embodiment wherein the amount of first drug administered is at least 40% less.

The above aspect of the invention includes an embodiment wherein the amount of first drug administered is at least 50% less.

The above aspect of the invention includes an embodiment wherein the amount of first drug administered is at least 60% less.

The above aspect of the invention includes an embodiment wherein the amount of first drug administered is at least 70% less.

The above aspect of the invention includes an embodiment wherein the amount of first drug administered is at least 80% less.

The above aspect of the invention includes an embodiment wherein the amount of first drug administered is at least 90% less.

The above aspect of the invention includes an embodiment wherein the first drug is fenfluramine and the indication be treated is appetite suppression.

The above aspect of the invention includes an embodiment wherein the CYP450 enzyme inhibitor is cannabidiol and the indication being treated is a refractory epilepsy.

The above aspect of the invention includes an embodiment wherein the refractory epilepsy selected is from the group consisting of Dravet syndrome, Lennox-Gastaut syndrome, and Doose syndrome.

These and other objects, advantages, and features of the invention will become apparent to those persons skilled in the art upon reading the details of treating epilepsy or a neurological condition by co-administering fenfluramine or a pharmaceutically equivalent salt thereof with one or more metabolic inhibitors, as more fully described below.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures FIG. 1 is a flow chart in tabular form detailing assessments and plasma sampling over each of three study periods during the clinical trial detailed in Example 1.

FIG. 4 is a schematic of the physiologically-based pharmacokinetic drug-drug interaction (PBPK DDI) model described in Example 2.

FIGS. 5A to 5E are time-course graphs showing changes in blood plasma levels of analytes in patients to whom were administered the following drugs alone or in combination: fenfluramine (0.8 mg/kg), stiripentol (2500 mg), clobazam (20 mg), or valproic acid (25 mg/kg to a max of 1500 mg). FIG. 5A is a time course graph of changes in blood plasma fenfluramine and norfenfluramine in subjects treated with 0.8 mg/kg of fenfluramine. FIG. 5B is a time-course graph showing changes in observed blood plasma levels of fenfluramine and norfenfluramine in subjects treated with 0.8 mg fenfluramine in combination with 3500 mg stiripentol, 20 mg clobazam, and 25 mg/kg (up to max 1500 mg) valproic acid. In both FIGS. 5A and 5B, observed data points from the study in Example 1 are superimposed over curves representing predicted fenfluramine and norfenfluramine exposure levels generated by running the PBPK DDI model described in Example 2. FIG. 5C is a time-course graph showing changes in observed blood plasma levels of clobazam in subjects given clobazam alone or in combination with fenfluramine. FIG. 5D is a time-course graph showing changes in observed blood plasma levels of stiripentol in subjects given stiripentol alone or in combination with fenfluramine. FIG. 5E is a time-course graph showing changes in observed blood plasma levels of valproic acid in subjects given valproic acid alone or in combination with fenfluramine. In all of FIGS. 5C, 5D, and 5E, observed data points from the study in Example 1 are superimposed over a curve representing predicted clobazam, stiripentol or valproic acid levels, respectively, generated by the PBPK DDI model described in Example 2.

FIG. 7 consists of charts 7A, 7B, 7C, 7D, 7E and 7F each of which shows clearance values for specified CYP450 enzymes considering the both renal excretion and hepatic metabolism, and indicate the relative contribution to overall clearance, based on literature reports and incubation studies using human liver microsomes. Clearance values are scaled as follows: blank indicates no contribution, + indicates minimal contribution, and ++ indicates partial contribution. Inhibition and induction values reflect the relative strength of an agent on enzyme activity, based on literature reports and data obtained from in vitro study results as well as the FDA Basic and Mechanistic Static Models, provided by the inventors. Inhibition and Induction values are scaled as follows: blank indicates no effects, 1 indicates weak effects, and 2 indicates strong effects.

DEFINITIONS

Figure 2:
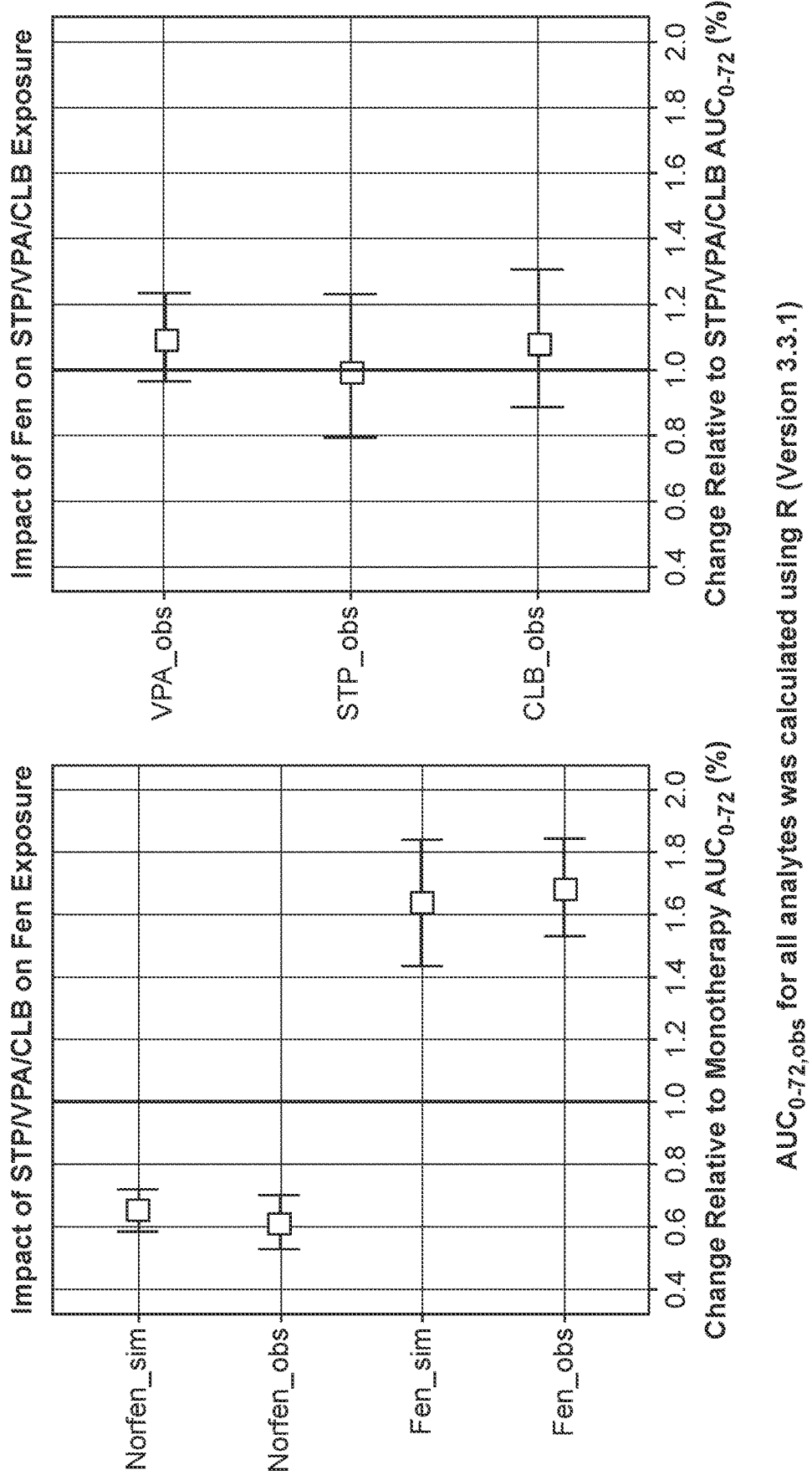
FIG. 2 consists of two bar charts showing the impact of co-administering fenfluramine with stiripentol, valproate and clobazam on blood plasma levels of fenfluramine and norfenfluramine in healthy subjects as described in Example 1.

As used herein, the term "subject" refers to a mammal. Exemplary mammals include, but are not limited to, humans, domestic animals (e.g., a dog, cat, or the like), farm animals (e.g., a cow, a sheep, a pig, a horse, or the like) or laboratory animals (e.g., a monkey, a rat, a mouse, a rabbit, a guinea pig, or the like). In certain embodiments, the subject is human.

As used herein, the terms "treatment," "treating," and the like, refer to obtaining a desired pharmacologic and/or physiologic effect. The effect can be prophylactic in terms of completely or partially preventing a disease or symptom thereof and/or can be therapeutic in terms of a partial or complete cure for a disease and/or adverse effect attributable to the disease. As used herein, the terms "treating," "treatment," "therapeutic," or "therapy" do not necessarily mean total cure or abolition of the disease or condition, and includes inhibiting the formation of potentially harmful drug metabolites. Any alleviation of any undesired signs or symptoms of a disease or condition, to any extent can be considered treatment and/or therapy. Furthermore, treatment can include acts that can worsen the patient's overall feeling of well-being or appearance. "Treatment," as used herein, covers any treatment of a disease in a mammal, particularly in a human, and includes: (a) preventing the disease from occurring in a subject which can be predisposed to the disease but has not yet been diagnosed as having it; (b) inhibiting the disease, i.e., arresting its development; and (c) relieving the disease, i.e., causing regression of the disease.

As used herein, the term pKa refers to the negative logarithm (p) of the acid dissociation constant (Ka) of an acid, and is equal to the pH value at which equal concentrations of the acid and its conjugate base form are present in solution.

As used herein, the term "fenfluramine active agent" refers to an agent that is at least in part a functional equivalent of fenfluramine. In some cases, the fenfluramine active agent is fenfluramine itself, or a pharmaceutically acceptable salt thereof. In some cases, the fenfluramine active agent is a structural derivative of fenfluramine. By "structural derivative" is meant a compound that is derived from a similar compound by a chemical reaction. In some cases, the fenfluramine active agent is a structural analog of fenfluramine, i.e., a compound that can in theory arise from another compound if one atom or group of atoms is replaced with another atom or group of atoms, regardless of whether that compound has been or could be synthesized using existing methods. In some cases, the fenfluramine active agent can be a structural analog of fenfluramine wherein one or more atoms are replaced with isotopes such as deuterium, 15N, and 13C.

As used herein, the term "metabolic enzyme" refers to any enzyme or biochemical pathway that transforms a molecule into another molecule, whether by chemical modification, conformational changes, or non-covalent association with another chemical species. The molecule resulting from the action of a metabolic enzyme is termed a "metabolite." Many metabolic enzymes and enzyme systems are known in the art, including but not limited to the cytochrome P450 or CYP450 enzyme system found in the liver, and glucuronosyltransferases found in the cytosol.

As used herein, the term "fenfluramine metabolizing enzyme" refers to any endogenous enzyme that acts on a fenfluramine or fenfluramine analog substrate in vivo to produce norfenfluramine or a de-alkylated norfenfluramine-type metabolite. Any convenient inhibitors of such metabolizing enzymes can be utilized in the subject methods and compositions to block metabolism of the fenfluramine active agent.

As used herein, terms such as "unwanted metabolites," "undesirable metabolites," and the like refer to metabolites that are not desired for any reason. "Harmful metabolites" are metabolites that are associated with one or more adverse effects. Illustrative examples of harmful metabolites are de-alkylated fenfluramine metabolites such as norfenfluramine, which activates the 5HT-2B receptor and are associated with heart valve hypertrophy. In general, harmful metabolites can act via any number of pathways and can be associated with any number of adverse effects.

"Clearance" as used herein refers to the process of removing a molecule from the body, and includes but is not limited to biochemical pathways which transform the molecule into its metabolites, and renal clearance.

DETAILED DESCRIPTION OF THE INVENTION

Before the present methods and compositions are described, it is to be understood that this invention is not limited to the particular methods and compositions described, as such can, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges can independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a compound" includes a plurality of such compounds and reference to "the method" includes reference to one or more methods and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided can be different from the actual publication dates which may need to be independently confirmed.

Overview

The basic concept behind the invention is to provide formulations and methods of treatment using combinations of certain drugs wherein a first drug which has known benefits is metabolized into a metabolite with adverse effects, wherein the first drug is administered with a second drug which inhibits metabolism of the first drug into the metabolite with adverse effects.

The invention is based on the surprising discovery that when certain first drugs having metabolites with adverse effects are co-administered with certain second drugs, patient exposure to the toxic metabolites are reduced while exposure to the first drug remains within therapeutic levels. In one exemplary combination, the first drug is a fenfluramine active agent, and the second drug is cannabidiol. When fenfluramine is administered in combination with cannabidiol, the formation of norfenfluramine is modulated down, while the blood plasma concentration of fenfluramine is maintained within therapeutic levels. In addition to the multidrug combination comprising fenfluramine and cannabidiol, other embodiments are contemplated and are disclosed herein.

An overall purpose of the drug combination is to make it possible to treat patients for a range of different diseases and conditions using the first drug while avoiding the adverse side effects of the metabolite of the first drug. A further purpose is to provide combination therapies wherein the second drug enhances the therapeutic efficacy of the first drug. A further purpose is to provide combination therapies wherein the second drug provides therapeutic benefits in addition to the therapeutic effects provided by the first drug.

The methods and multidrug combinations provided by the present invention and disclosed herein represent improvements over the prior art, in that they provide the advantage of improved patient safety as compared to methods and compositions which employ only the first drug. Further, certain embodiments of the methods and compositions provided by the present invention allow for decreased dosing of the first drug while maintaining efficacy that is equivalent to the efficacy provided by higher doses of the first drug when administered as a monotherapy. Further, certain embodiments of the methods and combination provided by the present invention allow for increased dosing of the first drug without increasing the safety risks associated with lower doses of the first drug when administered as a monotherapy. Further, certain embodiments of the methods and compositions provided by present invention show improved efficacy relative to the methods and compositions which employ only the first drug. Finally, certain embodiments of the methods and compositions provided by the present invention provide therapeutic effects apart from the therapeutic effects of the first drug.

Multidrug Combinations

Aspects of the invention provided by the present disclosure include multidrug combinations wherein a first drug which has known therapeutic benefits and which is metabolized into a metabolite with adverse effects, is administered with a second drug which inhibits the formation of the metabolite.

Therapeutic agents useful in the multidrug combinations of the present invention include fenfluramine active agents, including but not limited to fenfluramine and pharmaceutically acceptable salts thereof. Other therapeutic agents, including but not limited to fenfluramine structural analogs, are also contemplated.

As discussed above, and without being bound by theory, fenfluramine is metabolized by cytochrome P450 enzymes, including but not limited to CYP1A2, CYP2B6, CYP2C9, CYP2C19, CYP2D6, and CYP3A4, into norfenfluramine. As discussed above, and without being bound by theory, norfenfluramine is a 5HT2B agonist and is likely responsible for the adverse cardiac and pulmonary effects associated with the drug. Those effects can be reduced or eliminated by administering fenfluramine in combination with select second drugs that inhibits metabolism of fenfluramine into norfenfluramine, which down-modulates production of norfenfluramine. The net result is to increase the ratio of fenfluramine:norfenfluramine $AUC_{0-72}$ values in a manner that significantly decreases patient exposure to norfenfluramine while maintaining fenfluramine within therapeutic levels. The contributions of particular enzymes in overall clearance of those compounds, are presented in FIGS. 7A and 7B.

Thus, in one aspect the disclosure provides a multidrug combination wherein a fenfluramine is co-administered with a second drug that inhibits metabolism of fenfluramine into norfenfluramine by one or more CYP450 enzyme. In various embodiments, the second drug is an inhibitor of one or more of CYP1A2, CYP2B6, CYP2C8, CYP2C9, CYP2C19, CYP2D6, and CYP3A4. In various embodiments, the second drug is an inhibitor of CYP1A2. In various embodiments, the second drug is an inhibitor of CYP2B6. In various embodiments, the second drug is an inhibitor of CYP2C9. In various embodiments, the second drug is an inhibitor of CYP2C19. In various embodiments, the second drug is an inhibitor of CYP2D6. In various embodiments, the second drug is an inhibitor of CYP3A4.

A wide variety of antiepileptic drugs are inhibitors and inducers of metabolic pathways. The effects of selected agents are presented in FIGS. 7C to 7F. Stiripentol and clobazam are among the antiepileptic drugs most often used to treat Dravet syndrome. Stiripentol strongly inhibits CYP1A2, and CYP3A4, and also inhibits CYP2C9 and CYP2C19, albeit less strongly. See FIG. 7C, based on the European Medicines Agency European public assessment report review of Stiripentol (first published Jul. 1, 2009) Tran et al., Clin Pharmacol Ther. 1997 November; 62(5): 490-504, and Moreland et al., Drug Metab Dispos. 1986 November-December; 14(6):654-62. Clobazam is a weak inducer of CYP3A4. See FDA Approved Labeling Text for Onfi (clobazam) Tablets for oral use (Oct. 21, 2011). Further, there is evidence that clobazam strongly inhibits CYP2D6. See FIG. 7D.

Example 1 describes a clinical trial in which drug-drug interactions between fenfluramine and the anti-epileptic drugs stiripentol, clobazam, and valproate were studied in healthy volunteers. The results show that co-administering fenfluramine with these three drugs reduced patient exposure to norfenfluramine by nearly 30%, while increasing fenfluramine exposure by a factor of 1.67. See FIG. 2. These results demonstrate that the patient exposure to norfenfluramine can be significantly reduced by co-administering fenfluramine with metabolic inhibitors while fenfluramine is maintained within normal range.

Therefore, the present disclosure provides a multidrug combination wherein fenfluramine is administered with stiripentol, clobazam and valproate.

Figure 6:
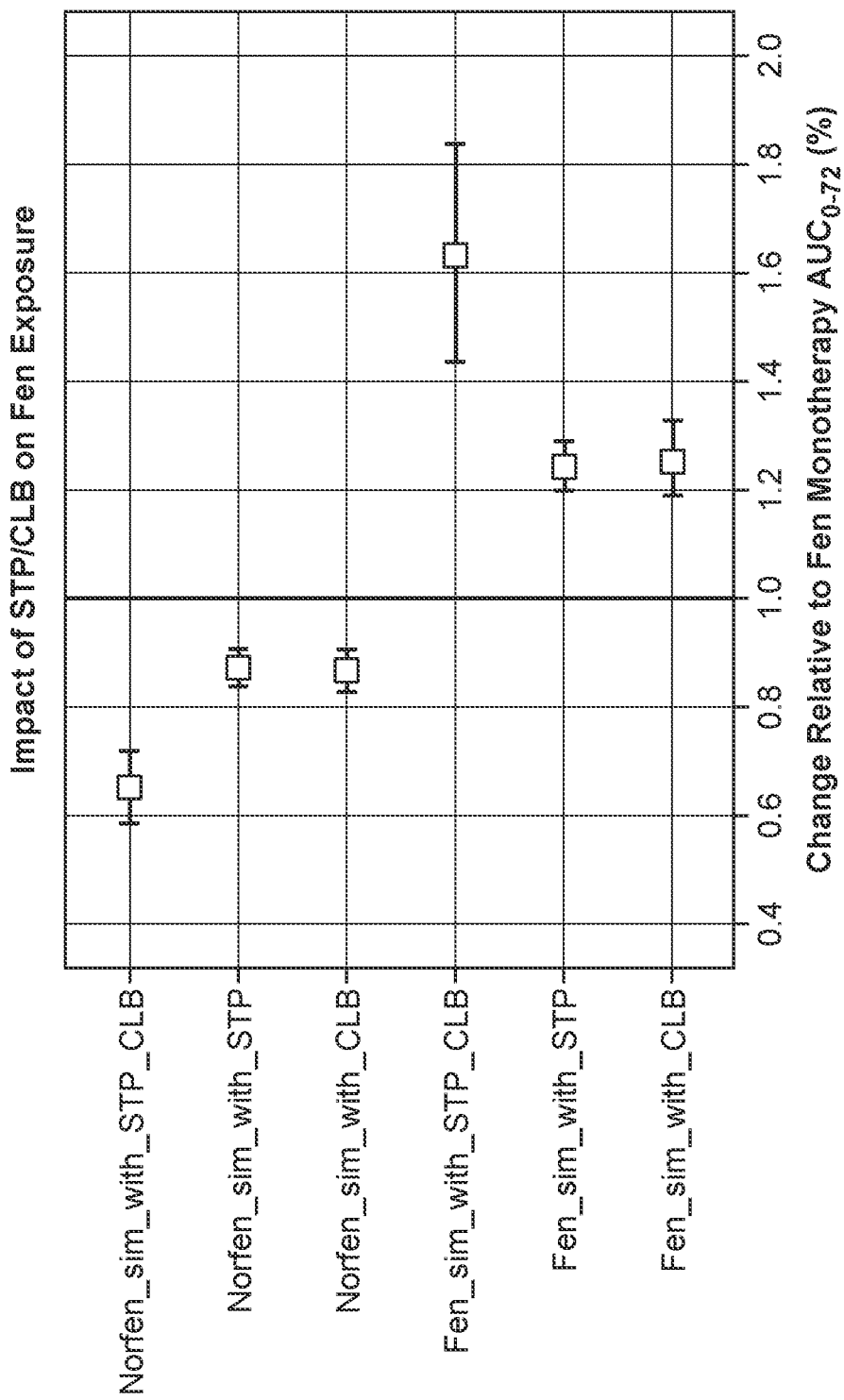
FIG. 6 compares the observed impact (% change relative to STP/VPA/CLB $AUC_{0-72}$) of co-administering fenfluramine with stiripentol, valproic acid, and clobazam on plasma levels of stiripentol, valproic acid, and clobazam with the impact on each drug predicted by the PBPK DDI model described in Example 2.

Example 2 describes the development and qualification of a physiologically-based pharmacokinetic ("PBPK") model for quantifying drug-drug interactions between fenfluramine and stiripentol, clobazam and valproate. See FIGS. 3 and 4. Results from model simulations show that co-administering fenfluramine with stiripentol alone, with clobazam alone, and with both stiripentol and clobazam together, significantly reduces patient exposure to norfenfluramine. See FIG. 6.

Therefore, the present disclosure provides multidrug combinations wherein fenfluramine is administered with a second drug selected from stiripentol, clobazam, and the combination of stiripentol and clobazam. In one exemplary embodiment, the multidrug combination comprises fenfluramine co-administered with stiripentol. In one exemplary embodiment, the multidrug combination comprises fenfluramine co-administered with clobazam. In one exemplary embodiment, the multidrug combination comprises fenfluramine co-administered with stiripentol and clobazam.

Recently, cannabidiol has been shown to exert inhibitory effects on several CYP450 enzymes. It is a potent inhibitor of CYP1A2 (time-dependent effect), CYP2B6, and CYP3A4, and has inhibitory effects on CYP2C8, CYP2C9, CYP2C19, and CYP2D6 as well. See FIG. 7F.

Example 3 details the refinement of the PBPK model described in Example 2 to provide the capability for simulating the impact of co-administering fenfluramine with cannabidiol, alone or in combination with other drugs, on fenfluramine and norfenfluramine exposure in patients to whom those drugs are co-administered. The model is qualified by comparing the changes in fenfluramine and norfenfluramine exposure predicted by the model with those observed in healthy volunteers.

Therefore, the present disclosure provides multidrug combinations wherein a first drug which is fenfluramine is co-administered with a second drug which is cannabidiol.

The multidrug combinations disclosed herein can further include one or more additional drugs in addition to the first and second drugs. The third or more drugs can be a metabolic inhibitor which further inhibits the formation of the harmful metabolite from the first drug (therapeutic agent), either by the same or different metabolic enzyme or pathway than the second, or an agent that provides further therapeutic benefits, e.g., by enhancing the efficacy of the first drug or providing additional therapeutic benefits, or an agent that is both a metabolic inhibitor and that provides further therapeutic benefits. Drugs of interest in this regard include, but are not limited to acetazolamide, barbexaclone, beclamide, brivaracetam, buprorion, cinacalet, clobazam, clonazepam, clorazepate, diazepam, divaloprex, eslicarbazepine acetate, ethadione, ethotoin, felbamate, gabapentin, lacosamide, lorazepam, mephenytoin, methazolamide, methsuximide, methylphenobarbitol, midazolam, nimetazepam, nitrazepam, oxcarbazepine, paramethadione, perampanel, piracetam, phenacemide, pheneturide, phensuximide, phenytoin, potassium bromide, pregabalin, primidone, retigabine, rufinamide, selectracetam, sodium valproate, stiripentol, sultiame, temazepam, tiagabine, topiramate, trimethadione, valnoctamide, valpromide, vigabatrin, zonisamide, and pharmaceutically acceptable salts thereof.

Methods

The present disclosure provides methods wherein a first drug which has known benefits is metabolized into a metabolite with adverse effects, wherein the first drug is administered with a second drug which inhibits the formation of the metabolite. Examples of drugs useful in practicing the invention are described above.

In one aspect, the present disclosure provides methods of administering a fenfluramine active agent to a subject in need thereof, e.g., for the treatment of a host suffering from a disease or condition treatable by a fenfluramine active agent (as described in greater detail herein). A further aspect of the subject methods is that the fenfluramine active agent is administered to the subject in combination with a second drug that inhibits the formation of norfenfluramine.

In one aspect, the multidrug combinations provided herein can be used to treat patients who suffer from or have been diagnosed with a diseases or disorder, or who experience symptoms for which they are in need of treatment, such as patients who have been diagnosed with a pediatric epileptic encephalopathies including but not limited to Dravet syndrome, Lennox-Gastaut syndrome, Doose syndrome, and West syndrome, or patients who experience pediatric refractory seizures, or patients susceptible to Sudden Unexpected Death in Epilepsy (SUDEP), or patients diagnosed with Alzheimers disease, and obesity. In one aspect, the multidrug combinations provided herein can be used to treat, reduce, or ameliorate the frequency and/or severity of symptoms associated with such diseases or disorders.

By "in combination with" or "in conjunction with", is meant that an amount of the metabolizing enzyme inhibitor is administered anywhere from simultaneously to about 1 hour or more, e.g., about 2 hours or more, about 3 hours or more, about 4 hours or more, about 5 hours or more, about 6 hours or more, about 7 hours or more, about 8 hours or more, about 9 hours or more, about 10 hours or more, about 11 hours or more, or about 12 hours or more, about 13 hours or more, about 14 hours or more, about 15 hours, about 16 hours or more, about 17 hours or more, about 18 hours or more, about 19 hours or more, about 20 hours or more, about 21 hours or more, about 22 hours or more, about 23 hours or more, about or 24 hours or more, prior to, or after, the fenfluramine active agent. That is to say, in certain embodiments, the fenfluramine active agent and metabolizing enzyme inhibitor are administered sequentially, e.g., where the fenfluramine active agent is administered before or after the metabolizing enzyme inhibitor. In other embodiments, the fenfluramine active agent and metabolizing enzyme inhibitor are administered simultaneously, e.g., where the fenfluramine active agent and metabolizing enzyme inhibitor are administered at the same time as two separate formulations, or are combined into a single composition that is administered to the subject. Regardless of whether the fenfluramine active agent and metabolizing enzyme inhibitor are administered sequentially or simultaneously, as illustrated above, or any effective variation thereof, the agents are considered to be administered together or in combination for purposes of the present invention. Routes of administration of the two agents can vary, where representative routes of administration are described in greater detail below.

In embodiments of the invention, any metabolizing enzyme inhibiting dose of the metabolizing enzyme inhibitor can be employed. Dosages for specific metabolic inhibitors are generally within a specified range, but will vary according to the factors which include but are not limited to the patient's age, weight, CYP2C19 metabolic activity, and the presence and degree of hepatic impairment. Such a dose is less than the daily dose of metabolizing enzyme inhibitor that leads to undesirable side effects.

Thus, for cannabidiol, a dose of about 0.5 mg/kg/day to about 25 mg/kg/day, such as less than about 0.5 mg/kg/day, about 0.6 mg/kg/day, about 0.7 mg/kg/day, about 0.75 mg/kg/day, about 0.8 mg/kg/day, about 0.9 mg/kg/day, about 1 mg/kg/day, about 2 mg/kg/day, about 3 mg/kg/day, about 4 mg/kg/day, about 5 mg/kg/day, about 6 mg/kg/day, about 7 mg/kg/day, about 8 mg/kg/day, about 9 mg/kg/day, about 10 mg/kg/day, about 1 mg/kg/day, about 12 mg/kg/day, about 13 mg/kg/day, about 14 mg/kg/day, about 15 mg/kg/day, about 16 mg/kg/day, about 17 mg/kg/day, about 18 mg/kg/day, about 19 mg/kg/day, about 20 mg/kg/day, about 21 mg/kg/day, about 22 mg/kg/day, about 23 mg/kg/day, about 24 mg/kg/day, to about 25 mg/kg/day, can be employed.

For clobazam, dosing is in accordance with FDA guidelines, with starting dosage, dose titration, and maximum dosage depending on the patient's body weight, tolerance, and response. Thus, for clobazam, a dose of about 5 mg/day to about 40 mg/day, such as about 5 mg/day, about 7.5 mg/day, about 10 mg/day, about 12.5 mg/day, about 15 mg/day, about 17.5 mg/day, about 20 mg/day, about 22.5 mg/day, about 25 mg/day, about 27.5 mg/day, about 30 mg/day, about 32.5 mg/day, about 35 mg/day, about 37.5 mg/day, to about 40 mg/day, can be employed For stiripentol, dosing is in accordance with FDA guidelines, with starting dosage, dose titration, and maximum dosage depending on the patient's body age, tolerance, and response. Thus, for stiripentol, a dose of about 20 mg/kg/day to about 50 mg/kg/day, such as about 20 mg/kg/day, 21 mg/kg/day, about 22 mg/kg/day, about 23 mg/kg/day, about 24 mg/kg/day, about 25 mg/kg/day, about 26 mg/kg/day, about 27 mg/kg/day, about 28 mg/kg/day, about 29 mg/kg/day, about 30 mg/kg/day, about 31 mg/kg/day, about 32 mg/kg/day, about 33 mg/kg/day, about 34 mg/kg/day, about 35 mg/kg/day, about 36 mg/kg/day, about 37 mg/kg/day, about 38 mg/kg/day, about 39 mg/kg/day, about 40 mg/kg/day, about 41 mg/kg/day, about 42 mg/kg/day, about 43 mg/kg/day, about 44 mg/kg/day, about 45 mg/kg/day, about 46 mg/kg/day, about 47 mg/kg/day, about 48 mg/kg/day, about 49 mg/kg/day, to about 50 mg/kg/day, can be employed.

As indicated above the dosing amounts of the metabolizing enzyme inhibitor can be based on the weight of the patient or can be preset in amounts that will vary with the inhibitor, for example expressed in microgram/day, mg/day or g/day or expressed as a dose administered more frequently or less frequently. In general, the smallest dose which is effective at inhibiting metabolism of the fenfluramine active agent should be used for the patient.

In general, known inhibitors have recommended dosing amounts. Those recommended dosing amounts are provided within the most current version of the Physician's Desk Reference (PDR) or http://emedicine.medscape.com/ both of which are incorporated herein by reference specifically with respect to any inhibitors and more specifically with respect to the dosing amounts recommended for those inhibitor drugs.

In connection with the present invention, the inhibitor can be used in the recommended dosing amount or can be used in a range of from about 1/100 to about 100 times, or from about 1/10 to about 10 times, or from about 1/5 to about 5 times, or from about 1/2 to about twice the recommended dosing amount, or any incremental 1/10 amount in between those ranges. Fenfluramine dosage can in some cases be determined relative to the dosage of the co-therapeutic agent with which it is administered, such that the patient's exposure to fenfluramine remains within a therapeutic range while the dosage of the co-therapeutic agent does not exceed recommended levels and/or minimizes or prevents unwanted side effects known to be associated with the co-therapeutic agent. For example, fenfluramine dosage can be calculated based on a molar or weight ratio of fenfluramine to the co-therapeutic agent. Fenfluramine dosage can be set according to the lowest dose that provides patient exposure within therapeutic levels when fenfluramine is administered with the co-therapeutic agent. Fenfluramine dosage can be set according to the highest dosage that provides patient exposure to norfenfluramine that does not exceed limits set by the FDA or which results in an increased risk that the patient will experience one or more serious adverse effects.

In connection with the present invention, fenfluramine can be used in the dosage amount recommended for fenfluramine administered in the absence of the co-therapeutic agent, or can be used in a range of from about 1/100 to about 100 times, or from about 10 to about 100 times, or from about 1/10 to about 10 times, or from about 1/5 to about 5 times, or from about 1/2 to about twice the recommended dosing amount, or any incremental 1/10 amount in between those ranges.

Stated differently and more specifically, fenfluramine can be used in the treatment of patients. For example, fenfluramine can be used in the treatment of patients with a form of epilepsy such as Dravet syndrome, Lennox-Gastaut syndrome, Doose syndrome or other refractory epilepsies and can also be used in appetite suppression. However, in any context where fenfluramine is used, it can be used in combination with an enzyme inhibitor such as cannabidiol and thereby reduce the dose of fenfluramine necessary in order to obtain a therapeutically effective result, and importantly reduce adverse side effects from the fenfluramine.

The therapeutically effective dose of fenfluramine is reduced when combined with cannabidiol. The reduction in the amount of the full therapeutic dose required to obtain a desired therapeutic effect is expected to be approximately 40%±5%. However, the reduction may be 10%, 20%, 30%, 40%, 50%, 60%, 70%, 80%, 90% or more when the fenfluramine is combined with cannabidiol (each ±5%).

This discovery that treating patients with the combination of fenfluramine and cannabidiol makes it possible to dramatically reduce the dose of fenfluramine, and thereby makes it possible to treat a wider range of patients with fenfluramine for a wider range of indications without adverse effects. With this particular combination, the inclusion of the cannabidiol makes it possible to reduce the amount of norfenfluramine (which is the metabolite of fenfluramine) which the patient is expose to, thereby reducing side effects.

Pharmaceutical Preparations

Also provided are pharmaceutical preparations. As used herein, pharmaceutical preparations mean compositions that include one or more compounds (either alone or in the presence of one or more additional active agents) present in a pharmaceutically acceptable vehicle. The term "pharmaceutically acceptable" means approved by a regulatory agency of the Federal or a state government or listed in the U.S. Pharmacopeia or other generally recognized pharmacopeia for use in mammals, such as humans. The term "vehicle" refers to a diluent, adjuvant, excipient, or carrier with which a compound of the invention is formulated for administration to a mammal.

The choice of excipient will be determined in part by the active ingredient, as well as by the particular method used to administer the composition. Accordingly, there is a wide variety of suitable formulations of the pharmaceutical composition of the present invention.

In one aspect, the present disclosure provides pharmaceutical preparation wherein the active agent is a fenfluramine active agent, i.e., fenfluramine or a pharmaceutically acceptable salt thereof. The dosage form of a fenfluramine active agent employed in the methods of the present invention can be prepared by combining the fenfluramine active agent with one or more pharmaceutically acceptable diluents, carriers, adjuvants, and the like in a manner known to those skilled in the art of pharmaceutical formulation. The dosage form of a metabolizing enzyme inhibitor employed in the methods of the present invention can be prepared by combining the enzyme inhibitor with one or more pharmaceutically acceptable diluents, carriers, adjuvants, and the like in a manner known to those skilled in the art of pharmaceutical formulation. In some cases, the dosage form of the fenfluramine active agent and the dosage form of a metabolizing enzyme inhibitor are combined in a single composition.

By way of illustration, the fenfluramine active agent and/or the metabolizing enzyme inhibitor can be admixed with conventional pharmaceutically acceptable carriers and excipients (i.e., vehicles) and used in the form of aqueous solutions, oils, oil- or liquid-based emulsions, tablets, capsules, elixirs, suspensions, syrups, wafers, sprinkles, and the like. Such pharmaceutical compositions contain, in certain embodiments, from about 0.1% to about 90% by weight of the fenfluramine active agent and/or the metabolizing enzyme inhibitor, and more generally from about 1% to about 30% by weight of the fenfluramine active agent and/or the metabolizing enzyme inhibitor. The pharmaceutical compositions can contain common carriers and excipients appropriate to the fenfluramine active agent or to the drugs co-administered with the fenfluramine agent, including carriers suitable for use with water-soluble drugs, such as corn starch or gelatin, lactose, dextrose, sucrose, microcrystalline cellulose, kaolin, mannitol, dicalcium phosphate, sodium chloride, and alginic acid, and carriers, and excipients suitable for use with drugs that are poorly miscible or immiscible in water, such as organic solvents, polymers, and others. Disintegrators commonly used in the formulations of this invention include croscarmellose, microcrystalline cellulose, corn starch, sodium starch glycolate and alginic acid.

Particular formulations of the multidrug combinations disclosed herein are in a liquid form. The liquid can be a solution, an emulsion, a colloid, or suspension, such as an oral solution, emulsion, or syrup. In an exemplary embodiment, the oral solution, emulsion, colloid, or syrup is included in a bottle with a pipette which is graduated in terms of the milligram amounts that will be obtained in a given volume of solution. The liquid dosage form makes it possible to adjust the solution for small children which can be administered anywhere from 0.1 mL to 50 mL and any amount between in tenth milliliter increments and thus administered in 0.1, 0.2, 0.3, 0.4 mL, etc.

A liquid composition will generally consist of a suspension, suspension or solution of the fenfluramine active agent and/or the metabolizing enzyme inhibitor or pharmaceutically acceptable salt in a suitable liquid carrier(s), for example, ethanol, glycerine, sorbitol, non-aqueous solvent such as polyethylene glycol, oils or water, with a suspending agent, preservative, surfactant, wetting agent, flavoring or coloring agent. Alternatively, a liquid formulation can be prepared from a reconstitutable powder.

Particular formulations of the invention are in a solid form.

Particular formulations of the invention are in the form of a transdermal patch.

EXAMPLES

The following examples are put forth so as to provide those of ordinary skill in the art with a complete disclosure and description of how to make and use the present invention, and are not intended to limit the scope of what the inventors regard as their invention, nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Drug-Drug Interaction Study: Effects of Co-Administering Fenfluramine with Stiripentol, Clobazam and Valproate on Plasma Levels of Fenfluramine and Norfenfluramine The effects of co-administration of a three-drug regimen on fenfluramine metabolism and resultant plasma levels of fenfluramine and its metabolite norfenfluramine was assessed in a clinical trial using in healthy volunteers. Interim results are reported below.

A. Trial Objectives and Design

A randomized, open-label, single-dose, 3-way cross-over study was designed to examine the effects of co-administering fenfluramine with a three-drug cocktail consisting of stiripentol, clobazam, and valproate. Each patient was treated sequentially with three treatment regimens, each being administered individually, according to six different treatment sequences which were assigned randomly.

| Agent | Dose | Regimen A | Regimen B (stiripentol regimen) | Regimen C |
|---|---|---|---|---|
| Fenfluramine | 0.8 mg/kg | X | X | |
| Stiripentol | 3,500 mg | | X | X |
| Clobazam | 20 mg | | X | X |
| Valproate | 25 mg/kg (≤1,500 mg) | | X | X |

| Treatment Sequence | Period 1 | Period 2 | Period 3 |
|---|---|---|---|
| 1 | A | B | C |
| 2 | B | C | A |
| 3 | C | A | B |
| 4 | C | B | A |
| 5 | A | C | B |
| 6 | B | A | C |

B. Selection of Subjects

Subjects were recruited from an existing pool of volunteers or through direct advertising, Prospects who had participated in a study within three months prior of dosing were excluded from the pool of potential participants. A full medical history for the preceding 12-month period was obtained from each subject's primary care physician and evaluated. Patients were then assessed according to the inclusion and exclusion criteria shown below. Persons chosen as study participants underwent a screening visit prior to participation to reassess and confirm compliance with those criteria.

1. Inclusion Criteria
    1. Healthy males.
    2. Non-pregnant, non-lactating healthy females.
    3. Age 18 to 50 years of age, inclusive.
    4. Body mass index within the range of 19.0 to 31.0 kg/mg2 and a minimum weight of 50.0 kg, inclusive, at screening, or if outside the range, considered not clinically significant by the investigator.
    5. Are medically healthy with no clinically significant condition that would, in the opinion of the investigator, preclude study participation, such as significant, renal endocrine, cardiac, psychiatric, gastrointestinal, pulmonary or metabolic disorders. Subjects should have no hepatic dysfunction.
    6. Have no clinically significant abnormalities in their clinical laboratory profile that would, in the opinion of the investigator, preclude study participation, including liver function tests outside of the normal range.
    7. Are non-smokers for at least 3 months (this includes e-cigarettes and nicotine replacement products) and test negative (<10 ppm) on a breath carbon monoxide test at screening and admission
    8. Must agree to use an adequate method of contraception.
    9. Female subjects of non-childbearing potential must be surgically sterile (e.g., tubal occlusion, hysterectomy, bilateral salpingectomy, as determined by subject medical history) or congenitally sterile, or at least 2 years post-menopause. Females of childbearing potential must use appropriate contraception.
    10. Able to speak, read, and understand English sufficiently to allow completion of all study assessments.
    11. Subjects must voluntarily provide written informed consent.
    12. Subjects, in the Investigator's opinion, must be able to complete study procedures.
    13. Must be willing to comply with the requirements and restrictions of the study.

Inclusion criteria 2 and 7 from the list above are re-assessed at admission/pre-dose.

2. Exclusion Criteria
    1. Women of childbearing potential who are pregnant or breastfeeding.
    2. Male subjects with pregnant partners
    3. Have uncontrolled blood pressure (BP), i.e., subject has a supine systolic BP>160 mmHg or <90 mmHg, and/or a supine diastolic BP>100 mmHg or <40 mmHg at screening or admission.
    4. Have an oxygen saturation <92% on room air.
    5. Have hypersensitivity or idiosyncratic reaction to fenfluramine, stiripentol, clobazam or valproic acid.

C. Assessments

An overview of study procedures is provided in the trial flow chart table presented in FIG. 1.

D. Results

Interim results of the drug-drug (DDI) study are shown in FIG. 2. $AUC_{0-72}$ values were calculated based on blood plasma levels of fenfluramine and norfenfluramine levels. Exposure impact is expressed as a ratio of $AUC_{0-72}$ values determined for patients receiving the combination treatment to the $AUC_{0-72}$ values determined for patients receiving fenfluramine alone. Those results show an increase in patient exposure to fenfluramine by a factor of 1.66 and a decrease in norfenfluramine exposure by a factor of 0.59 when fenfluramine is co-administered with a combination of stiripentol, clobazam, and valproic acid.

Example 2

Development & Qualification of a Physiologically-Based Pharmacokinetic ("PBPK") Model for Predicting Drug-Drug Interactions A physiologically-based pharmacokinetic (PBPK) model able to quantify potential drug-drug interactions (DDI) and facilitate dose justification for clinical trials of fenfluramine (FEN) was developed, qualified, and then used to predict the impact of co-administering one or more anti-epileptic drugs (AED), specifically stiripentol (STP), valproic acid (VPA) and clobazam (CLB).

A. Model Development

Figure 3:
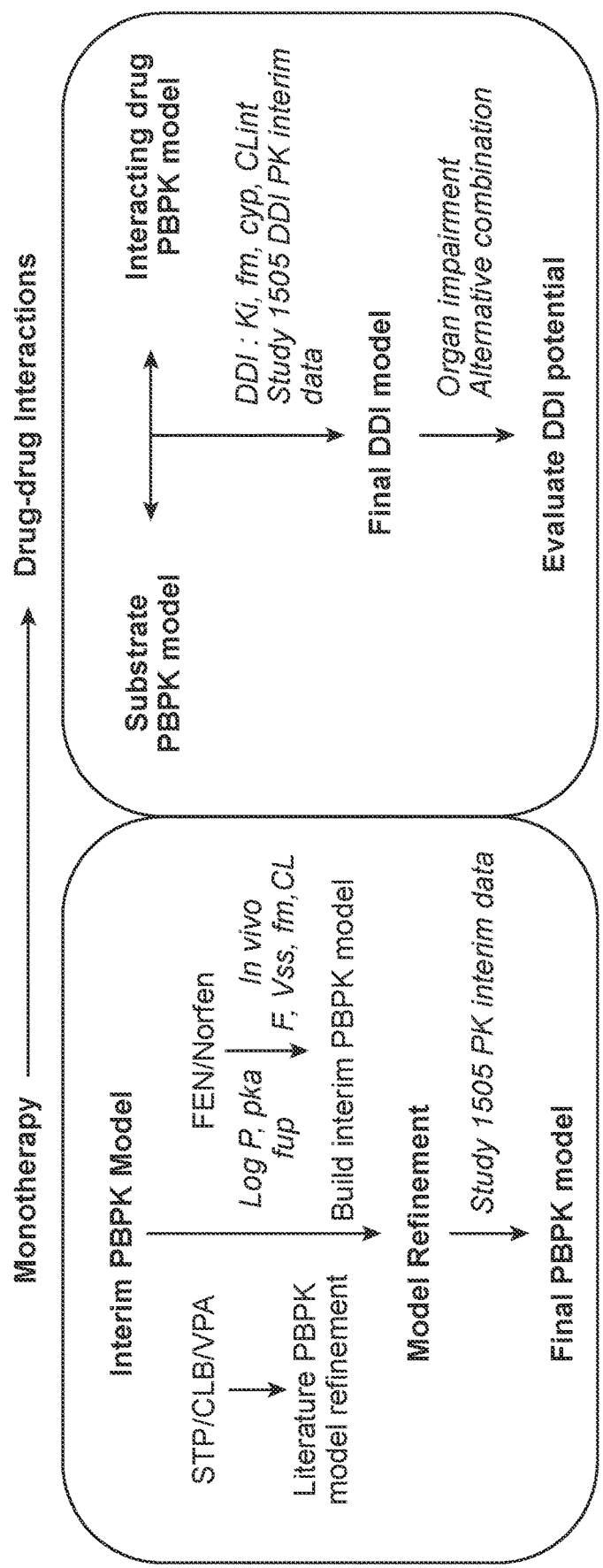
FIG. 3 is a flow chart diagramming the development of the physiologically-based pharmacokinetic drug-drug interaction (PBPK DDI) model described in Example 2.
Figure 5E:
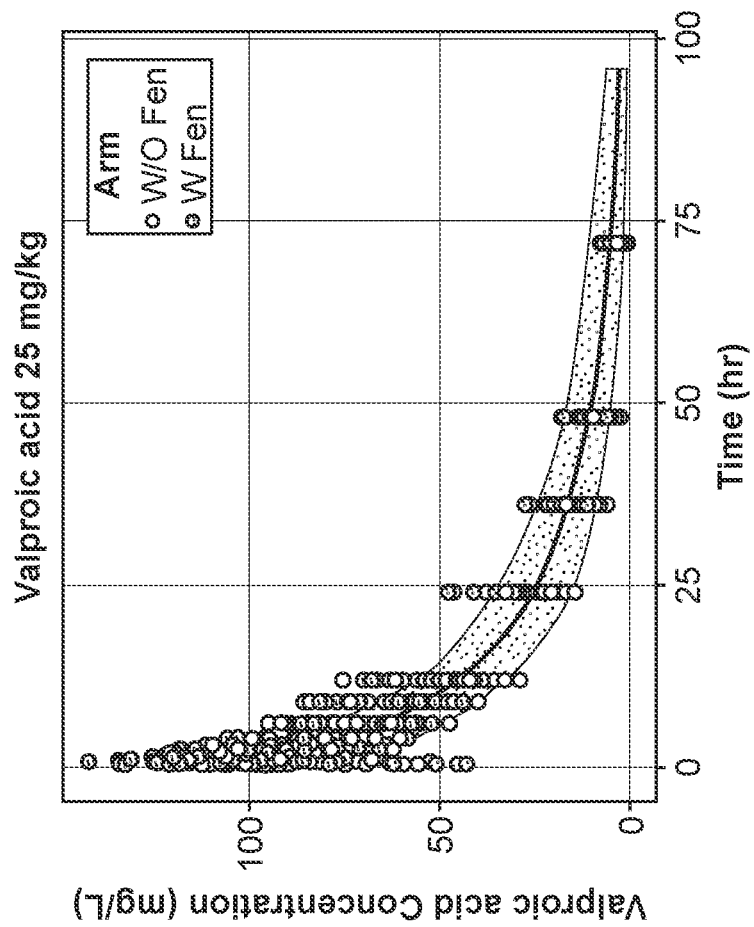

See FIGS. 3 and 4. The PBPK models for the concomitant medications were developed by refining published PBPK models from the literature; the model for fenfluramine was developed de novo using basic properties of the molecule (fraction unbound, pKa, etc.). Drug interactions were accounted for by adjusting the simulated metabolic enzyme efficiencies at each simulated time point according to the concomitant medication concentration in the liver at that time point. PBPK models accounted for age-dependent factors such as blood flow, tissue volume, glomerular filtration rate, CYP maturation, hepatic intrinsic clearance, and bioavailability. Each model was comprised of ten perfusion-limited tissues.

Tissue-to-plasma coefficients for FEN and its metabolite norfenfluramine (norFEN) were calculated by integrating physiochemical and in vitro properties such as Log P, pKa, and fup; See Xenobiotica (2013) 43:839). FEN was eliminated by renal excretion and hepatic metabolism; 76% of hepatic intrinsic clearance ($CL_{int}$) was converted into nor-FEN. See Arch Int Pharmacodyn Ther, (1982) 258:15, and J Pharmacy Pharmacol (1967) 19:49S.

The STP PBPK model was developed by the refinement of a published PBPK model, in which STP was eliminated solely via liver metabolism. See Pharm Res (2015) 32:144. Refinement involved the incorporation of a secondary elimination route of renal clearance into the system. Both the CLB and the VPA PBPK models were developed by refinement of previously published models. See Pharm Res (2015) 32:144 and Eur J Pharm Sci (2014) 63:45.

For the drug-drug interaction, the inhibitory effects of stiripentol and clobazam on FEN elimination were described by reversibly inhibiting CYP1A2, CYP3A4, CYP2C9, CYP2C19, and CYP2D6-mediated hepatic metabolism based on the liver concentrations of the concomitant medications. Model development was conducted in Berkeley Madonna (v 8.3.18).

The hepatic intrinsic clearance of FEN in combination ($CL_{int,\ DDI}$) can be calculated as $$\frac{CLint_{,DDI}}{CLint} = \frac{fm_{,CYP1A2}}{1+\frac{C_{STP,liv}}{K_{I,1A2}}} + \frac{fm_{,CYP2D6}}{1+\frac{C_{CLB,liv}}{K_{I,2D6}}} + \frac{fm_{,other}}{1+\frac{C_{STP,liv}}{Ki_{,other}}} + fm_{,CYP2B6}$$

Where $fm_{,other}$ includes $fm_{,CYP3A4}$ and $fm_{,CYP2C19}$

B. Model Qualification

The model was qualified by comparing the changes in fenfluramine and norfenfluramine exposure observed in the study described in Example 1 above with the effects predicted by the model. FIGS. 5A through 5E show that predicted changes in blood plasma levels of fenfluramine, norfenfluramine, stiripentol, clobazam and valproic acid are in close agreement with the changes observed in healthy volunteers, thereby demonstrating the model's robustness.

C. Predicted Effects of Co-Administering Fenfluramine with One or Both of Clobazam and Stiripentol on Blood Plasma Levels of Fenfluramine and Norfenfluramine The PBPK DDI model was used to predict the impact of co-administering fenfluramine with one or both of stiripentol and clobazam. Results are presented in FIG. 6.

Example 3

Extrapolation and Refinement of the PBPK Model to Include Cannabidiol Effects on Fenfluramine Exposure The model developed as described in Example 2 is further refined to provide the capability to simulate the impact of co-administering FEN with cannabidiol (CBD), alone or in combination with other drugs, on fenfluramine and norfenfluramine exposure. In particular, the model described in Example 2 is amended to account for cannabidiol's inhibitory effects on metabolic enzymes that metabolize fenfluramine, i.e. CYP1A2, CYP2B6, CYP2C9, CYP2C19, CYP2D6, and CYP3A4, and the time-dependency of CBD's inhibitory effects on CYP1A2.

Example 4

Extrapolation and Refinement of the PBPK Model to Include Cannabidiol Effects on Fenfluramine Exposure The effects of co-administration of a two-drug regimen comprising fenfluramine and cannabidiol on fenfluramine metabolism and resultant plasma levels of fenfluramine and its metabolite norfenfluramine is assessed in a clinical trial using healthy volunteers according to the protocol described in Example 1, with the exception that stiripentol and clobazam are replaced with cannabidiol, administered at a dose of 10 mg/day and 25 mg/day, respectively. Patients receiving fenfluramine are dosed at either 0.2 mg/kg/day or 0.8 mg/kg/day.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A method of reducing or ameliorating seizures in a patient, comprising:
    administering fenfluramine; and
    administering cannabidiol thereby modulating down formation of norfenfluramine, and resulting in higher levels of fenfluramine.

2. The method of claim 1, wherein the patient is diagnosed with Dravet syndrome.

3. The method of claim 1, wherein the patient is diagnosed with a form of refractory epilepsy selected from the group consisting of Dravet syndrome, Lennox-Gastaut syndrome, Doose syndrome, and West syndrome.

4. The method of claim 1, further comprising:
co-administering to the subject an effective amount of a co-therapeutic agent selected from the group consisting of acetazolamide, barbexaclone, beclamide, brivaracetam, buprorion, cinacalet, clobazam, clonazepam, clorazepate, diazepam, divaloprex, eslicarbazepine acetate, ethadione, ethotoin, felbamate, gabapentin, lacosamide, lorazepam, mephenytoin, methazolamide, methsuximide, methylphenobarbitol, midazolam, nimetazepam, nitrazepam, oxcarbazepine, paramethadione, perampanel, piracetam, phenacemide, pheneturide, phensuximide, phenytoin, potassium bromide, pregabalin, primidone, retigabine, rufinamide, selectracetam, sodium valproate, stiripentol, sultiame, temazepam, tiagabine, topiramate, trimethadione, valnoctamide, valpromide, vigabatrin, zonisamide, and pharmaceutically acceptable salts thereof.

5. A method of reducing or ameliorating seizures in a patient diagnosed with a form of refractory epilepsy, comprising:
administering a liquid formulation of fenfluramine to the patient in an amount in the range of 0.2 mg/kg/day to 0.8 mg/kg/day; and
administering cannabidiol in a liquid formulation in an amount of 0.5 mg/kg/day to 25 mg/kg/day thereby modulating down formation of norfenfluramine, and resulting in higher levels of fenfluramine.

6. A method of reducing or ameliorating seizures in a patient diagnosed with a form of refractory epilepsy, comprising:
administering a liquid formulation of fenfluramine to the patient in an amount which is 30% less than an effective amount in the range of 0.2 mg/kg/day to 0.8 mg/kg/day, due to co-administration of cannabidiol in a liquid formulation in an amount of 0.5 mg/kg/day to 25 mg/kg/day thereby modulating down formation of norfenfluramine, and resulting in higher levels of fenfluramine.

7. The method of claim 6, wherein the fenfluramine is administered in an amount of 70% less than an effective dose of 0.8 mg/kg/day.

8. The method of claim 6, wherein the fenfluramine is administered in an amount of 0.56 mg/kg/day or less.

9. A method of reducing or ameliorating seizures patient diagnosed with Dravet syndrome, comprising:
administering a liquid formulation of fenfluramine to the patient in an amount in the range of 0.2 mg/kg/day to 0.8 mg/kg/day; and
administering cannabidiol in a liquid formulation in an amount of 0.5 mg/kg/day to 25 mg/kg/day thereby modulating down formation of norfenfluramine, and resulting in higher levels of fenfluramine.

10. A method of reducing or ameliorating seizures in a patient diagnosed with Dravet syndrome, comprising:
administering a liquid formulation of fenfluramine to the patient in an amount which is 40% less than an effective amount in the range of 0.2 mg/kg/day to 0.8 mg/kg/day, due to co-administration of cannabidiol in a liquid formulation in an amount of 0.5 mg/kg/day to 25 mg/kg/day thereby modulating down formation of norfenfluramine, and resulting in higher levels of fenfluramine.

* * * * *